United States Patent [19]

Toyama et al.

[11] 4,247,698
[45] Jan. 27, 1981

[54] RED COLORING COMPOSITE AND THE METHOD FOR ITS PRODUCTION

[75] Inventors: Ryosuke Toyama, Kobe; Hiroyuki Inoue, Kyoto; Tetsuro Shingu, Nishinomiya; Yoshio Takeda, Tokushima; Takeshi Ikumoto, Kobe; Hidetoshi Okuyama, Kobe; Osamu Yamamoto, Kobe, all of Japan

[73] Assignee: Taito Co., Ltd., Tokyo, Japan

[21] Appl. No.: 88,725

[22] PCT Filed: Aug. 9, 1979

[86] PCT No.: PCT/JP78/00054
§ 371 Date: Aug. 9, 1979
§ 102(e) Date: Aug. 9, 1979

[87] PCT Pub. No.: WO 79/00394
PCT Pub. Date: Jul. 12, 1979

[30] Foreign Application Priority Data

Dec. 15, 1977 [JP] Japan .................. 52-151145

[51] Int. Cl.³ .......................... C07D 221/02
[52] U.S. Cl. ......................... 546/112; 8/646; 8/401; 260/345.2; 536/4; 536/22
[58] Field of Search ............... 8/53, 85 R; 536/4; 546/112; 260/345.2

[56] References Cited

FOREIGN PATENT DOCUMENTS 5106230  7/1974  Japan .
52-53934  4/1977  Japan .
53-134824  11/1978  Japan .

Primary Examiner—A. Lionel Clingman

[57] ABSTRACT

Novel reddish coloring compounds of varying hue and the method for its production, obtained by reaction between iridoid compounds contained in biological substances, where if necessary, by pretreatment with chemical or enzymic means to form —COOH at the C-4 position, and in the case of glycosides by hydrolysis of iridoid compounds to aglycones with chemical or microbial or enzymic means, and a substance possessing a primary amino group under acidic condition.

4 Claims, 2 Drawing Figures

RED COLORING COMPOSITE AND THE METHOD FOR ITS PRODUCTION

Technological Field

The present invention relates to a red coloring composite and a method for its production wherein the red coloring composite is the reaction product between substances of iridoid compounds having a carboxyl (—COOH) group at the C-4 position of the iridoid skeleton, or compounds obtained by hydrolysis of the compounds having methoxycarbonyl (—COOCH₃) group at the C-4 position, or a mixture of above compounds and substances containing a primary amino group.

BACKGROUND OF THE INVENTION

The present inventors have disclosed a method for producing blue coloring composite obtained, firstly, by the application of a microorganism to the extract of gardenia fruits (*Gardenia jasminoides* var. *grandiflora*) (Japanese Patent Application Publication No. 13971/1977), and secondly by the application of a primary amino group-containing substance to the aglycones of iridoid glycosides (Japanese Patent Application No. 130131/1975), and have elucidated the mechanism for the formation of these coloring compounds and their structures (Japanese Patent Application No. 49418/1977). Further studies revealed that the red coloring composite, with maximum absorption at 520–540 nm, is formed between iridoid compounds where, if necessary, by application of microorganism or enzyme, or chemical method, either alone or in combination, in the case of glycosides to obtain the aglycone, and substances containing a primary amino group. Physicochemical properites of these coloring composite were investigated and the present invention was completed.

DESCRIPTION OF THE INVENTION

The present inventors have already reported in the Specifications of the afore-mentioned Japanese Patent Applications that the aglycone of iridoid glycosides represented by geniposide easily reacts with a primary amino group; that is, addition of a substance having a primary amino group to iridoid compounds possessing a partial structure of

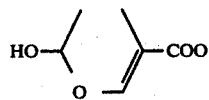

with ultraviolet absorption at 230–240 nm results in facile substitution of oxygen atom with nitrogen atom in the primary amino group to form a skeleton having a partial structure containing nitrogen atom,

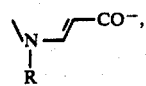

and the conjugated system is further extended by the effect of lone-pair electrons of the introduced nitrogen atom to form a blue substance with an absorption maximum at 580–600 nm in the visible region.

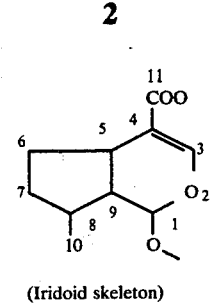

(Iridoid skeleton)

According to the present invention, however, application of a substance containing a primary amino group, under acidic condition, to the aglycone of iridoid compounds having a carboxyl group (COOH) at the C-4 position of the iridoid skeleton resulted in the formation of the red coloring composite with absorption maximum at 520–540 nm in the visible region, although its reaction mechanism still remains unknown. This method can further be applied to iridoid compounds possessing a methoxy-carbonyl group (—COOCH₃) at the C-4 position. The conventional method used for the hydrolysis of esters, such as the application of acid or alkali (including treatment with ion-exchange resin), or enzyme, easily affords iridoid compounds with —COOH group at the C-4 position from compounds with —COOCH₃ group at the C-4 position. When they are present as glycosides, they can be hydrolyzed to yield the aglycone and then, the aglycone reacts with a substance possessing a primary amino group under acidic condition (preferably in the presence of an organic acid) to produce red coloring composite. It was also found that the hue of coloring composite can be controlled by selecting the kinds of primary amines and iridoid compounds, and by changing the conditions of the reaction.

BEST FORM FOR PRACTICE OF THIS INVENTION

Figure 1:
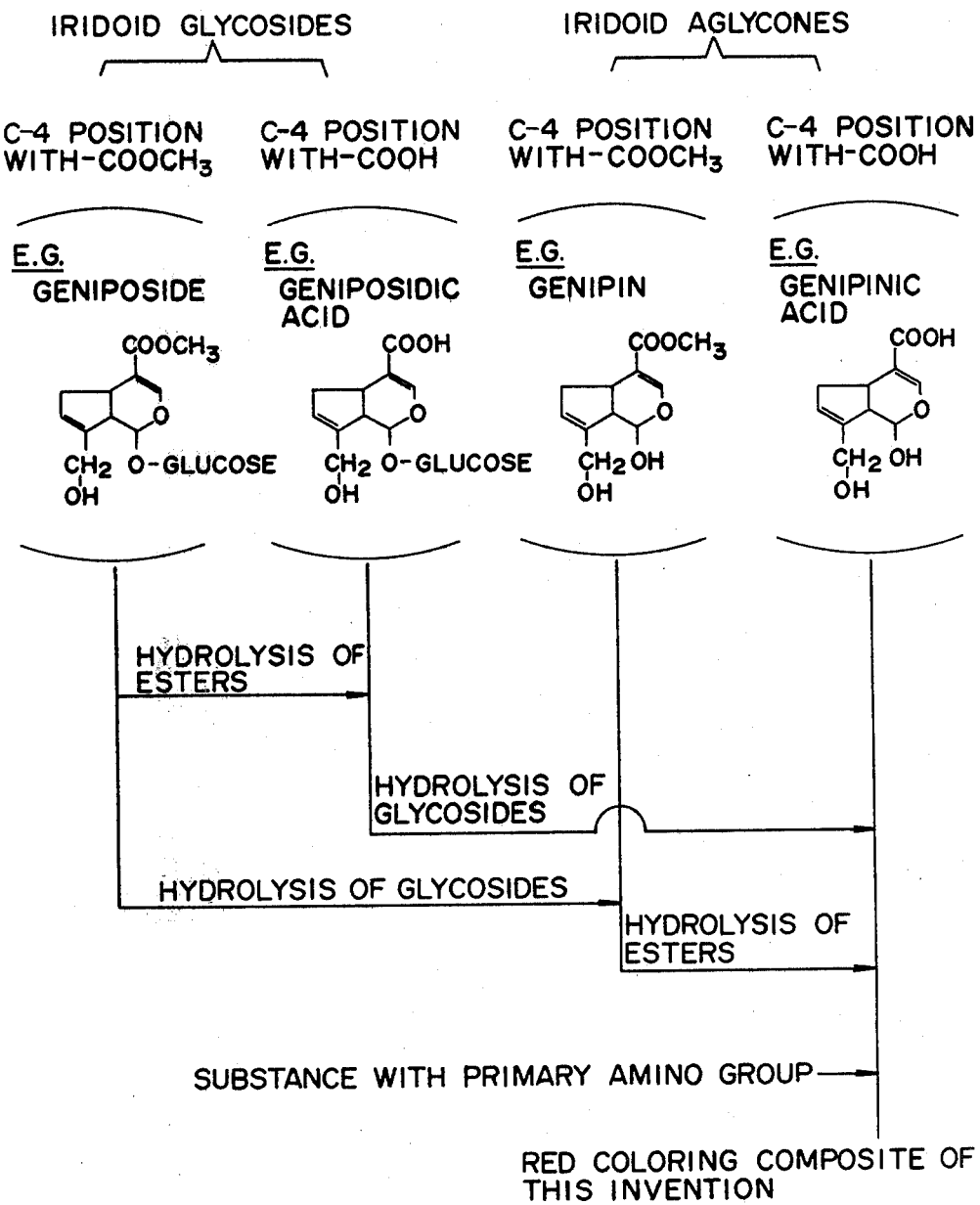
FIG. 1 shows the schematic mode of the present invention.

The Claims of the present invention cover red coloring composite having absorption maximum at 520–540 nm in the visible region by the application of a substance having a primary amino group to iridoid compounds themselves or mixtures containing them, and the method for the production of the red coloring composite. For example, in the case of producing red coloring composite from the fruits of *Gardenia jasminoides* Ellis and *Genipa americana* Linn., which contain iridoid compounds, the following method can be adopted. The fruits of *Gardenia jasminoides* and *Genipa americana* contain a number of iridoid compounds; some of them, like geniposidic acid, possess —COOH group at the C-4 position of the iridoid skeleton, while there are a large amount of substances like genipin and geniposide that possess —COOCH₃ group at the C-4 position. Therefore, these esters must be hydrolyzed by some appropriate methods to convert all the iridoid compounds present to those having a —COOH group at C-4 position, and the modified iridoid compounds reacting on the primary amine will give the red coloring composite with good yield. At first, alkaline solution, OH-type ion-exchange resin, and/or an enzyme with esterase activity, either alone or in combination, is applied to the extracts of the fruits of gardenia or genipa to hydrolyze the esters. Then the acid, microorganism, or enzyme with $\beta$-glucosidase activity, either alone or in combination, is applied to the iridoid glycosides contained in the extracts to obtain the aglycones. Treatment of these aglycones with a substance possessing a primary amino group will afford the red coloring composite. This reaction for the formation of the coloring composite does not require strictly limited conditions except for adjustment of pH to acidity, and coloring composite with varying hue can be manufactured under suitable conditions. For example, the extract of gardenia fruits is treated with alkaline solution to change C-4 position of iridoid glycosides to —COOH form, and the solution is adjusted to pH 4.0 with acetic acid or citric acid to effect enzymic hydrolysis of the next step. Protein and crocetin which precipitate at this stage are removed from the solution. An enzyme with $\beta$-glucosidase activity and an amino acid like glycine as the substance possessing a primary amino group are added to the solution, and the sugar moiety is hydrolyzed under optimal condition with the action of enzyme, and then inactivation of this solution by heating result in the formation of a clear red solution of a coloring composite with the aid of clarification process. Deproteinization of the above-mentioned precipitate formed at pH 4.0 will give crocetin of high purity. The properties of red coloring composite obtained by this invention varies according to the amine used and conditions of the reaction adopted from red to reddish purple. The color of coloring composite thus obtained have excellent heat, light and pH stabilities preservability and dyeability. Solubility can be varied by choosing the substance possessing a primary amino group to be incorporated, such as soluble in water hydrophilic organic solvents, or soluble in hydrophobic organic solvents. There are many possibilities for the application of the coloring composite of this invention. For example, there are possibilities of using it as a food color after toxicity tests, and as a dyestuff and pigment.

EXAMPLE I 1 mmol of geniposide dissolved in 10 ml of 0.5 N sodium hydroxide solution was stirred at room temperature for 3 hrs, and then pH was adjusted to 4.0 with acetic acid, and the total volume was brought to 20 ml with water. A small amount of $\beta$-glycosidase and 2 eq. of a substance possessing amino group were added to this solution and the solution was allowed to stand at 40° C. over night. This solution was inactivated by heating and coloring composite thus obtained was filtered and the visual comparison of color was listed in Table 1.

TABLE 1

| Nitrogen-containing compound used | Color |
|---|---|
| Glycine | Red |
| Glycine methyl ester | Red |
| Monomethylamine | Reddish purple |
| Dimethylamine | — |
| Trimethylamine | — |
| Arginine hydrochloride | Reddish purple |
| Glucosamine hydrochloride | Reddish purple |
| Glutamic acid | Red |
| Glycylglycine | Reddish purple |

TABLE 1-continued

| Nitrogen-containing compound used | Color |
|---|---|
| Soybean protein | Reddish purple |
| No nitrogenus compound added (control) | — |

EXAMPLE II

Figure 2:
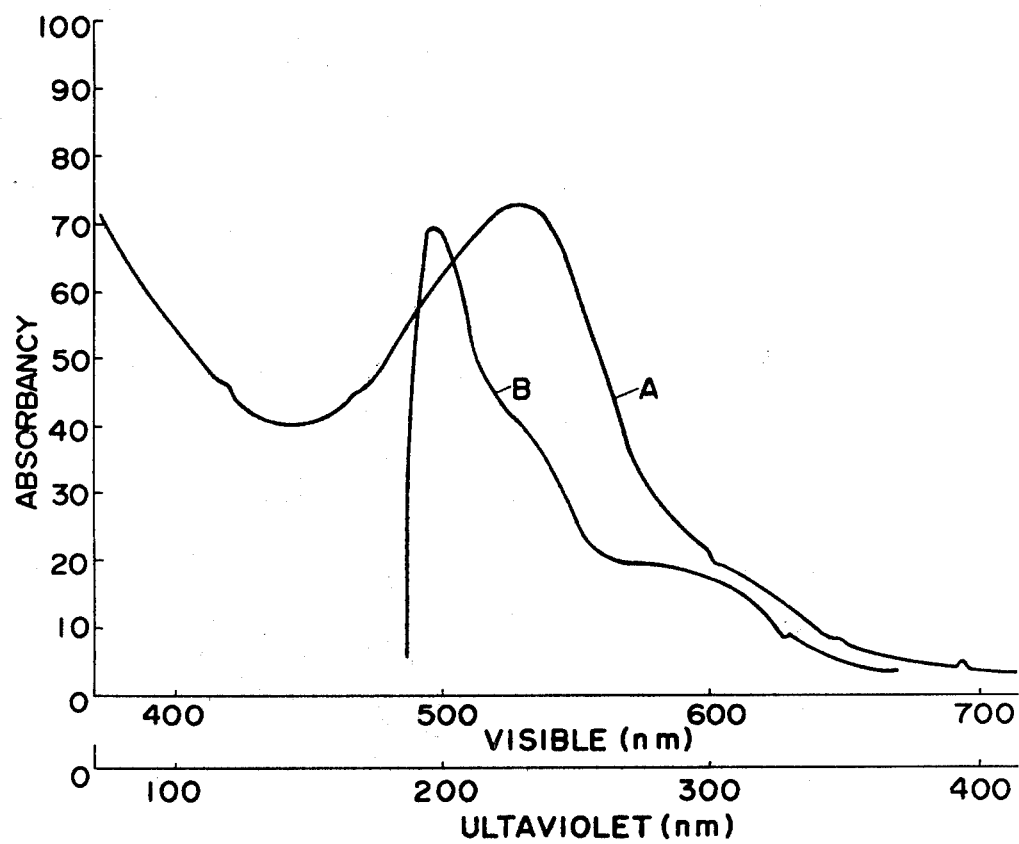
FIG. 2 shows the absorption curves in the visible region (A) and that in the ultraviolet region (B) of the solution of red coloring composite produced according to Example II to be described later.

Gardenia fruit was extracted with aqueous methanol, and 500 g of the concentrated extract (ca. 50% solid) was passed through a column filled with 1 kg of granular activated carbon. The column was washed first with water, and then developed with a mixture of water and methanol with increasing concentration of methanol. The fractions eluted with 30% methanol were evaporated under reduced pressure to yield 650 mg of crude geniposidic acid. A solution of 300 mg of this crude geniposidic acid dissolved in 10 ml of acetate buffer (pH 4.8), added with $\beta$-glucosidase, was allowed to stand over night at 37° C. to hydrolyze geniposidic acid. The aglycone thus formed was extracted with ether, the extract was evaporated under reduced pressure, and 90 mg of residue was obtained. This residue was dissolved in 10 ml of 50% aqueous ethanol, and after pH was adjusted to 4.0 with acetic acid, 100 mg of glycine was added, and the mixture was heated at 90° C. for 1 hr to obtain red coloring composite. Absorption spectra of this colored solution in the visible and ultraviolet regions are shown in FIG. 2.

EXAMPLE III

After obtaining fractions of 30% methanol in Example II, the column was further eluted with increasing concentration of methanol and the fractions obtained from 70% to 100% methanol were combined and the eluate was evaporated to dryness under reduced pressure. Recrystallization of the residue from ethanol gave 40 g of geniposide. A solution of 15 g of geniposide in 300 ml of 0.5 N sodium hydroxide was stirred at room temperature for 3 hrs to hydrolyze the ester, and inorganic materials were removed by treatment with ion-exchange resin (Amberlite IR-120, H+ form). The solution thereby obtained was passed through a column of activated carbon, and after developing the column with methanol, the effluent was concentrated under reduced pressure. To 4 g of the residue thus obtained, 1.5 g of alanine and 0.02 g of emulsion ($\beta$-glucosidase) were added together with 100 ml of acetate buffer of pH 4.5, and the mixture was allowed to stand at 37° C. for 40 hrs to effect hydrolysis of the glycoside. By heating this mixture at 95° C. for 1 hr, water-soluble red coloring composite was produced in the solution.

EXAMPLE IV

The fruit of *Genipa americana* was extracted with 1 N sodium hydroxide solution and the extract was treated with ion-exchange resin (Amberlite IR-120, H+ form) to remove inorganic matter in the extract. This solution was evaporated under reduced pressure to obtain concentrate with 73% solid. A 100 ml medium consisting of 2% of this concentrate, 0.5% of peptone, 0.3% of beef extract, and 2% of starch was poured into each 500-ml flask, and the flasks were sterilized at 120° C. for 20 min. One platinum loop of *Aspergillus niger* ($\beta$-glucosidase-producing organism) was inoculated into each flask, and the flasks were cultured with shaking at 30° C. After 100 hrs, the red coloring composite was produced in the medium and this medium was heated at 120° C. for 20 min for sterilization and the insoluble and suspending matters were removed by centrifugation. The clear solution thus obtained was passed through a membrane filter of 0.45 μm pore size, and aqueous solution containing water-soluble red coloring composite was obtained.

The same result is obtained by the use of gardenia fruits in place of *Genipa americana* used in this Example.

EXAMPLE V 24 g of the concentrated ethanol extract (75% solid) of gardenia fruits dissolved in 120 ml of 1 N sodium hydroxide solution was stirred at 50° C. for 5 hrs, and the solution was adjusted to pH 4.0 by the addition of 50% citric acid of aqueous solution, and the mixture was centrifuged, by which crocetin in gardenia fruits was separated as precipitate. The mixture of clear solution thus obtained, 1.5 g of glycine, 1.5 g of cellulase AP5 (Amano Seiyaku Co., Ltd.), and 19 ml of water, was allowed to stand at 50° C. for 16 hrs, then heated at 95° C. for 1 hr, and was filtered off the insoluble matter to obtain 170 ml of clear red solution of coloring composite (absorbancy of 83 at 530 nm).

POSSIBILITY OF INDUSTRIAL APPLICATION

The novel red coloring composite of this invention was derived from natural sources and low toxic red coloring matter is expected by screening through toxicity tests. It is possible to use this composite as a dyestuff and pigment for clothes, plastic materials, and printing ink, and as a food color for foodstuff, meat products, fishery processed goods, cakes, beverages, and alcoholic drinks, and as a red coloring matter for medicinals and cosmetics.

We claim:

1. Red coloring composite characterized by being obtained by application of a substance possessing a primary amino group to iridoid compounds possessing —COOH group at the C-4 position of the iridoid skeleton, or to iridoid compounds obtained by hydrolysis of substances possessing —COOCH$_3$ group at the C-4 position, or to the substances containing such mixed compounds as final structure of —COOH at the C-4 position.

2. A process for production of red coloring composite characterized by the application of a substance possessing a primary amino group to iridoid compounds possessing —COOH group at the C-4 position of the iridoid skeleton, or to iridoid compounds obtained by hydrolysis of substances possessing —COOCH$_3$ group at the C-4 position, or to the substances containing such mixed compounds as final structure of —COOH at the C-4 position.

3. A process of production given in claim 2 wherein the hydrolysis of —COOCH$_3$ at the C-4 position of the iridoid skeleton is carried out by the enzymic action, microbial action, or chemical method, either alone or in combination.

4. A process of production given in claim 2 wherein the substances possessing primary amino groups are amino acids, proteins, amino-sugars, or their related substances.

* * * * *